United States Patent [19]

Baldwin et al.

[11] Patent Number: 4,977,282

[45] Date of Patent: Dec. 11, 1990

[54] PRODUCTION OF D-ALPHA-TOCOPHEROL FROM NATURAL PLANT SOURCES

[75] Inventors: William S. Baldwin; Stephen M. Willging; Brock M. Siegel, all of Minneapolis, Minn.

[73] Assignee: Henkel Corporation, Ambler, Pa.

[21] Appl. No.: 337,599

[22] Filed: Apr. 13, 1989

Related U.S. Application Data

[62] Division of Ser. No. 601,194, Apr. 17, 1984, abandoned.

[51] Int. Cl.$^5$ .............................................. C07D 311/72
[52] U.S. Cl. ...................................... 549/412; 549/413
[58] Field of Search ................................. 549/412, 413

[56] References Cited

U.S. PATENT DOCUMENTS 2,519,863   8/1950   Weisler ................................. 549/412

*Primary Examiner*—Nicky Chan
*Attorney, Agent, or Firm*—Ernest G. Szoke; Wayne C. Jaeschke; Patrick J. Span

[57] ABSTRACT

Quantities of natural tocopherol can be aminoalkylated to selectively introduce functional groups onto the 5 and 7 positions of the non-alpha-tocopherol homologues. Natural d-alpha-tocopherol can then be separated from the aminoalkylated non-alpha-tocopherols as salts. After separation the adducts can then be reduced by hydrogenolysis, thereby upgrading vitamin E activity by making d-alpha-tocopherol out of the intermediate tocopherol adducts. Salts of these adducts can be crystallized by contacting the adducts with phosphoric acid. Salts will form upon acetic acid addition, and the delta-tocopherol adduct acetate can be isolated as a crystalline solid. The adducts can also be regenerated from the salts and transformed to alpha-tocopherol by reduction of the adduct.

17 Claims, 1 Drawing Sheet

PRODUCTION OF D-ALPHA-TOCOPHEROL FROM NATURAL PLANT SOURCES

This application is a division, of application Ser. No. 06/601,194 filed Apr. 17, 1984, abandoned.

BACKGROUND OF THE INVENTION

This invention relates to the isolation of high purity, natural d-alpha-tocopherol which is produced abundantly in nature, and which is the E vitamin of greatest activity. It also relates to the enhancement of the Vitamin E activity of a concentrate of mixed tocopherol homologues including beta-, delta- and gamma-tocopherols and which could include tocotrienols, which can be derived from natural plant sources. The instant invention achieves the separation of the beta-, delta- and gamma- homologues in high purity from the alpha-tocopherol; recovering the alpha-tocopherol and methylating the beta-, gamma- and delta- homologues to provide additional high purity alpha-tocopherol.

The term Vitamin E was originally used to designate the active component of certain vegetable oils. Vitamin E activity means the physiological activity of a group of nutrient materials originally isolated from various natural sources. The materials having Vitamin E activity all belong to a distinct series of compounds which are all derivatives of chroman-6-ol. These compounds are all tocol derivatives having an isoprenoid $C_{16}$-side chain. The term "tocol" is used to mean 2-methyl-2-(4',8',12'-trimethyltridecyl) chroman-6-ol. The compounds of primary importance for Vitamin E activity are the methylated tocols, especially 5,7,8-trimethyl tocol. The nomenclature currently used for this compound is alpha-tocopherol; 5,8-dimethyl tocol is betatocopherol; 7,8-dimethyl tocol is gamma-tocopherol, and 8-methyl tocol is delta-tocopherol. The tocopherol nomenclature will be used throughout.

The physiological activity of this group of compounds is measured by the ability to maintain fertility in rats. The Vitamin E active compounds have a variety of beneficial effects in humans with the alpha-tocopherol homologue having the highest potency as measured by its effectiveness in maintaining rat fertility. For this reason the term Vitamin E is frequently used interchangeably with d-alpha-tocopherol, the naturally occurring tocopherol of highest Vitamin E activity.

Alpha-tocopherol can also be prepared synthetically, although in commercial synthetic preparations the product is always present in admixture with its 1-homologue as racemic dl-alpha-tocopherol, which according to present nomenclature is designated as all-rac-alpha-tocopherol, and is a mixture of 8 stereoisomers.

Alpha-tocopherol is produced commercially for use as a feed supplement for domestic animals as a source of Vitamin E activity and as a nutrient supplement for humans. Tocopherols are also used in food technology as an anti-oxidant to retard the development of rancidity in fatty materials.

The tocopherols are found widely distributed in normal foods, occurring in the highest concentration in the cereal grain oils, principally in corn and wheat oils, but also in barley and rye. They are also found in vegetable oils such as safflower, soybean, peanut, cottonseed, linseed, sunflower, rapeseed and palm, and in other vegetable sources, e.g. palm leaves, lettuce, alfalfa, rubber latex and a variety of other plant materials. The proportion of the most active form, the d-alpha-tocopherol varies widely among the different sources. Two of the highest sources of dalpha-tocopherol is safflower oil and sunflower oil, though the most commonly available source is soybean oil, which has a considerably lower percent of d-alpha-tocopherol with significantly higher percentages of the gamma- and deltahomologues. In addition to being a source for tocopherol homologues, palm oil, oats, rye, and barley also contain tocotrienol.

The naturally occurring tocopherols are generally isolated from natural products such as vegetable oil sources by various combinations of such procedures as esterification, saponification, extraction, distillation, ion-exchange, adsorption chromatography, precipitation of sterols, crystallization, and many others. The tocopherol concentrate isolated in this manner will vary depending on the particular vegetable source and separation techniques used. Generally however, the concentrate is a mixture of tocopherol homologues containing about 40% or more impurities such as residual sterols, hydrocarbons, and fatty acids. This concentrate containing up to about 60% mixed tocopherol homologues is suitable for further processing to produce dalpha-tocopherol of 90% or greater purity. The non-alphatocopherols in the mixture can be converted to the more biologically active d-alpha-tocopherol by introducing methyl substituents into the aromatic ring (Tocol ring). A variety of ways are known for achieving this upgrading. The methylation can be done by halomethylation, aminomethylation, hydroxy-alkylation or formylation to introduce a methyl functional group followed by reduction to give the methylated tocopherol.

Various prior art alkylation methods are known, including aminoalkylation as described for example in Weisler U.S. Pat. Nos. 2,486,539 and 2,519,863. These methods are generally applied to low potency tocopherols extracted from plant sources by reacting the mixed tocopherols with an amino-alkylating agent, suitably piperidine hydrochloride and paraformaldehyde in an ethanol solvent acidified with hydrochloric acid. The amino alkyl addition product of mixed tocopherols is then reduced by catalytic hydrogenation to convert the non-alpha tocopherols in the mixture to alpha-tocopherol. Other alkylation methods, e.g. haloalkylation are also known. The haloalkylation reaction is preferably a chloromethylation achieved by reaction of the non-alpha-tocopherols present with a solution of formaldehyde in the presence of a hydrogen halide such as hydrogen chloride. This results in the introduction of a chloromethyl group. Other chloroalkyl groups may be introduced by using the corresponding aldehydes. This chloromethyl group is converted into a methyl group by a reduction procedure using stannous chloride and hydrochloric acid. Zinc and HCl reduction may also be employed instead of stannous chloride which is preferred. A simultaneous chloromethylation and reduction may be conducted in a single step by adding the stannous chloride to the initial reaction mixture thereby producing the methylation in a single stage process.

Other methods of alkylating tocopherols include the formylation methods described in U.S. Pat. No. 2,592,531 in which mixed tocopherols are reacted with formaldehyde in the presence of an organic acid catalyst. More recently, Japanese Patent No. 79-143,054 describes a process for preparing alpha-tocopherol from mixed tocopherols by reacting with formaldehyde and a reducing agent in the presence of an organic acid, to convert the non-alpha-tocopherols directly to alpha-tocopherol by hydroxymethylating and reducing in a single stage. Other acid catalysts such as phosphoric and boric acid can also be utilized as shown in U.S. Pat. Nos. 3,819,657 and 3,338,922.

All of these prior art methods generally involve converting the non-alpha-tocopherols in the mixture to alphatocopherols along with the alpha-tocopherol originally present in the mixture as high potency d-alpha-tocopherol. None of these methods involve separating the d-alpha-tocopherol from its beta-, gamma- and delta- homologues and thereafter upgrading only the mixture of non-alpha-tocopherol homologues to the high potency d-alpha-tocopherol form.

It has now been found, that by aminoalkylation of mixed tocopherols the amino adducts of the non-alpha-tocopherol homologues are provided, which can be readily separated from any alpha-tocopherol. The sterol and hydrocarbon impurities also present in the mixed tocopherol starting materials remain with the original alpha-tocopherol fraction. Alphatocopherol can be recovered in high purity by separating from the sterol and hydrocarbon impurities, without having to handle also the homologue tocopherols. Furthermore, the homologue materials which are obtained from the separation in high purity can be readily converted to the d-alpha-form in high yield and high purity. Moreover, it should be noted that this invention can be used to isolate the naturally produced d-alpha-tocopherol, and to upgrade the natural nonalpha-tocopherols present.

Accordingly, it is an object of this invention to provide a method for separating natural d-alpha-tocopherol from plant materials containing a mixture of tocopherol homologues. It is a further object of this invention to provide a method for separating d-alpha-tocopherol from a mixture of alpha-, and one or more of its beta-, gamma- and deltahomologues by reacting the mixture with a reagent which forms with the beta-, gamma- and delta- homologues derivatives that can be readily separated from the unreacted alpha-tocopherol present in the mixture. Yet another object of the invention is to prepare salts of the amine adducts of beta-, gamma- and delta-tocopherols which can be readily isolated from a mixture containing alpha-tocopherol.

Still another object is to provide new intermediates in the conversion of beta-, gamma- and delta-tocopherols to alpha-tocopherol. Still another object of the invention is to provide novel methods for methylating beta-, gamma- and delta-tocopherols. These and other objects can be more fully understood from the following description and working embodiments which are more fully set out below.

FIG. 1 represents a flow diagram showing the isolation and production of d-alpha-tocopherol from natural plant sources.

DETAILED DESCRIPTION

Figure 1:
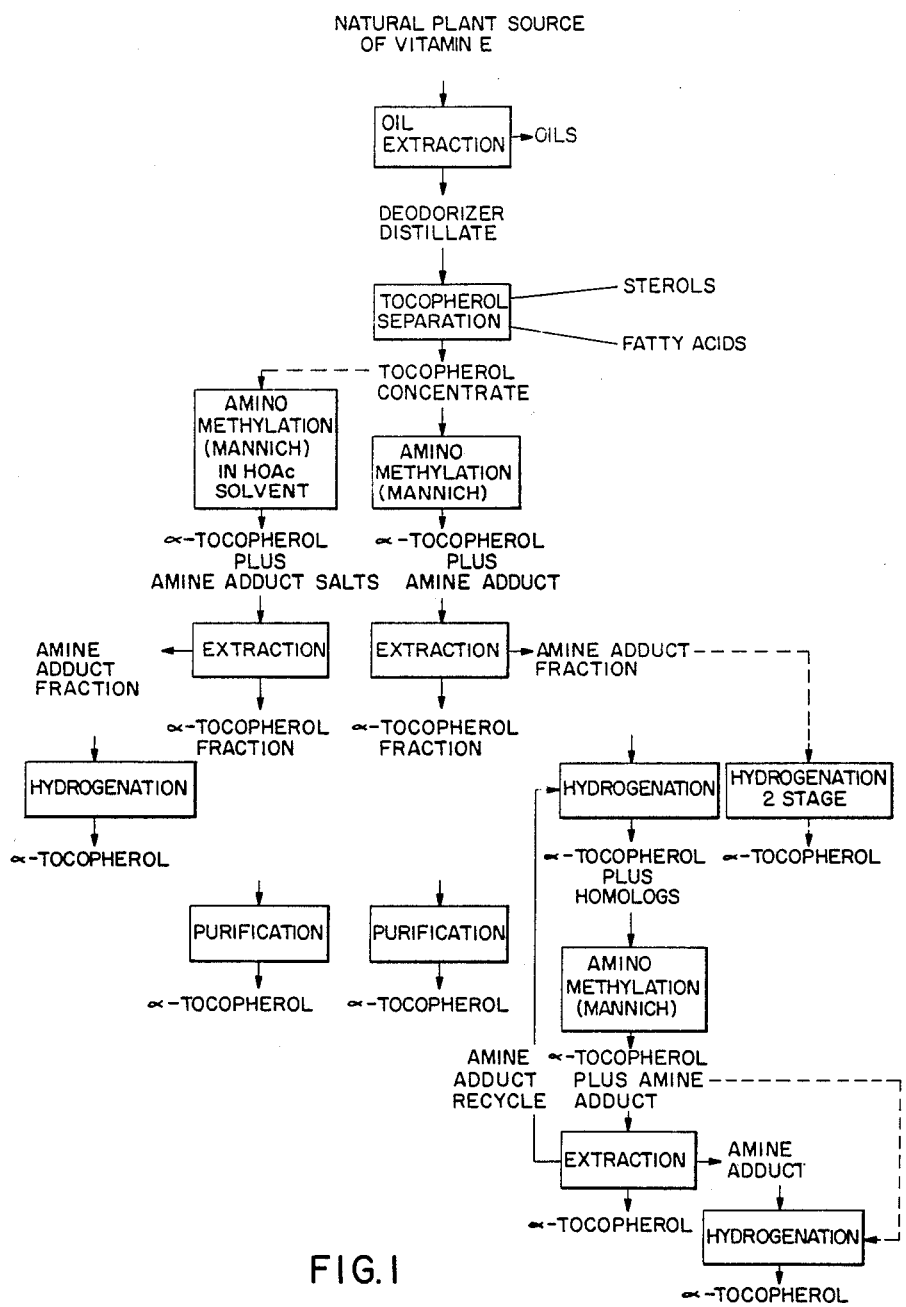

In its broad aspect this invention comprises the recovery of natural d-alpha-tocopherol from natural plant sources by first reacting the mixture with suitable reagents which will react with the non-alpha-tocopherols to introduce a functional group in the 5 and/or 7 positions of the tocopherol homologues, (the numbering of the carbon atoms is in accordance with the accepted system for identifying positions on the Tocol ring). Thereafter, unreacted naturally occurring alpha-tocopherol, having no functional group, is separated from the homologues which now carry the added functional group. Any convenient separation method utilizing the difference in properties imparted by the particular functional group can be used, (i.e. by extraction, precipitation, distillation, chromatography, or the like). It is possible, with this invention, to isolate alpha-tocotrienol and to upgrade the non-alpha- tocotrienols to alphatocopherol. In a preferred embodiment the functional group is such that it can be reduced to a methyl substituent by hydrogenolysis, so that lower potency beta-, gamma- or delta- homologues present can be more easily upgraded to the higher potency d-alpha-tocopherol. In another embodiment the invention provides novel methods for converting low potency beta-, delta- and gamma-tocopherols to the preferred d-alpha-tocopherol homologues, particularly the 2-R, 4'R, 8'R stereo-homologue also designated as d-alpha-tocopherol.

This invention includes a process for the separation of d-alpha-tocopherol from a mixture of d-alpha-tocopherol, and aminoalkylated tocopherol homologues. This is accomplished by a process comprising: contacting the mixture containing the d-alpha-tocopherol with a water miscible polar solvent containing an acid and a water immiscible, non-polar solvent also insoluble in the polar solvent whereby two phases are formed having the aminoalkylated tocopherol adducts in the polar, water miscible phase, and the alpha-tocopherols in a non-polar, water immiscible phase and separating the phases. This process permits the isolation of the naturally produced d-alpha-tocopherol and, with the addition of an aminomethyl group to the 5 and 7 positions of the non-alpha-tocopherols the non-alpha-tocopherols can be upgraded to d-alphatocopherol tocopherol of the same vitamin effectiveness and molecular structure as the naturally produced d-alpha-tocopherol.

The aminomethylation, also known as the Mannich reaction, is an effective method to achieve separation capabilities since the aminomethylated tocopherol adducts are capable of being upgraded to the d-alpha-tocopherol. This reaction is accomplished at temperatures from room temperature up to 130° C. for a sufficient length of time to cause the aminomethyl addition. The reagents necessary are formaldehyde and an amine.

The invention can be understood most easily by reference to FIG. 1, which shows the process steps applicable to the inventive process. This invention deals with, in particular, the treatment of tocopherol containing materials; preferably with tocopherol concentrate such as shown in FIG. 1. In this embodiment a mixture of tocopherol homologues is reacted with ammonia, primary or secondary amine which will enable the separation of the natural d-alpha-tocopherol. Representative, but non-exhaustive examples of such amines are: cyclic and aromatic amines, alkyl amines, polyamines. Particular examples of more suitable amines are methylamine, dimethylamine, and morpholine. Most preferred is dimethylamine to form a mixture containing alpha-tocopherol plus the amine adducts of the non-alpha-tocopherol homologues. Any mixture of tocopherol homologues, including alpha-tocopherol, and at least one of the beta-, gamma- or delta- homologues in any proportion can be used as the starting material.

Any oil having a tocopherol content is suitable starting material for the process of the instant invention. Oils containing as little as 3% by weight alpha-tocopherol with an additional amount of mixed tocopherol homologues are suitable for the process of the instant invention. The material may also include tocotrienol, which can also be upgraded. Even an oil with little to no alpha content can have the non-alpha-tocopherol content converted to a more biologically active d-alpha-tocopherol by the addition of the amine, followed by reduction, as described within the process of the instant invention which results in the introduction of methyl groups to the aromatic ring.

The preferred starting material for the process of this invention is a mixed tocopherol concentrate obtained from soyabean oil deodorizer distillate. The tocopherol distribution of soyabean oil is generally from about 3 to 20% alpha-, from about 45 to 60% gamma-, and from about 20 to 30% by weight delta-tocopherol. The deodorizer distillate may also contain tocopherol residues from processing other vegetable oils, for example wheat germ oil, the tocopherol distribution of which is from about 50 to 60% alpha-, and from about 25 to 40% beta-tocopherol. The deodorizer distillate, raw material usually containing from about 5 to 20% mixed tocopherols, or even higher concentrations may be used, to provide a suitable starting material for the amination reaction. Although it is possible to use material having as little as 5% tocopherol content.

Methods for isolating and concentrating tocopherols from plant sources are known in the art and the product from any of these methods can be employed. For example, by known methods a deodorizer distillate is produced from alkali refined soyabean oil containing about 0.2% mixed tocopherols (alpha-, gamma-, and delta-) by distilling in a molecular still and collecting the tocopherol fraction which distills below 240° C. at 0.004 mm Hg. Sterols and other substances are removed from the tocopherol fraction by crystallization from acetone. In this method, the glycerides are removed by saponification, and the unsaponified portion is further concentrated by a second molecular distillation to yield a mixed tocopherol fraction containing at least about 60% total mixed tocopherols.

Naturally produced d-alpha-tocopherol is recovered free from its homologues by reacting the mixture of tocopherols with an appropriate reagent to introduce a functional group at the 5 and/or 7 positions of the non-alpha-tocopherol homologues. The functional group permits the homologues to be separated from the natural d-alpha-tocopherol. Preferred reagents will introduce a substituted methyl group, allowing the thus substituted homologues to be readily reduced to dalpha-tocopherol after separation of unreacted naturally produced d-alpha-tocopherol.

A preferred functional group added to the non-alphatocopherol which allows both an easy separation of the nonalpha-tocopherol adduct intermediate is the aminomethyl group, and is added to non-alpha-tocopherol homologues by the preferred aminoalkylation reaction (also known as the Mannich reaction). Any amine suitable for a Mannich reaction can be used to achieve this and although it is possible to use any one of many available aldehydes, in order to introduce the substituted methyl groups, formaldehyde or any substance which produces formaldehyde, such as paraformaldehyde, must be used. The aminoalkylation reaction preferably utilizes an amine of the formula:

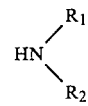

wherein $R_1$ and $R_2$ are each independently selected from a group consisting of hydrogen, polyamines, or an aliphatic hydrocarbon of one to about 8 carbon atoms; or wherein $R_1$ and $R_2$ together with the nitrogen atom can form a substituted or unsubstituted nitrogen heterocycle, such as morpholine, pyrrolidine, piperidine or piperidine bearing one or more of the usual substituents on the ring carbons such as lower alkyl, halo, and the like. The aliphatic hydrocarbon groups may be any cyclic or acyclic, straight or branched chain, saturated or unsaturated hydrocarbons. The lower alkyl groups, suitably methyl, ethyl, propyl or isopropyl having 1 to 4 carbon atoms are, however, preferred. Especially preferred are the dialkyl amines, particularly dimethylamine.

In carrying out the aminomethylation (Mannich) reaction, the relative molar concentration of the formaldehyde and the amine are acceptably maintained in equimolar amounts since they react on a 1 to 1 basis. Their relative concentrations can be varied, however, as long as there is at least one mole of formaldehyde, and one mole of amine for each mole of tocopherol present. Moreover, the reaction can be done with excess amounts of formaldehyde and the amine. Preferably, the formaldehyde and the amine are maintained in equimolar amounts relative to each other but in excess relative to the total tocopherol equivalents present in the mixed tocopherol concentrate. As long as the formaldehyde and amine are in excess relative to the tocopherol it is not critical that they be present in equimolar amounts relative to each other. Either may be present in an amount of from about 1 to 20 moles per mole of tocopherol. Suitably the formaldehyde and amine are both present in a molar amount of at least 1.5 times greater than the amount of tocopherol present. The tocopherols, the amine, and the aldehyde are combined, and the mixture is heated to a temperature of from room temperature to about 130° C. for a minimum of 15 minutes, after which the unreacted reagents are removed. If desired, an aldehyde other than formaldehyde, e.g. acetaldehyde, propionaldehyde and the like may be used, in which case the corresponding amino ethyl, aminopropyl and the like adducts are obtained. If an aldehyde other than formaldehyde was used, the tocopherol adducts may not be reduced directly into d-alpha-tocopherol, but instead, must have the functional group removed before the addition of the methyl group can upgrade the vitamin E activity. The amine adducts of the non-alpha-tocopherols obtained in the reaction are then separated from the unreacted alpha-tocopherol.

It has been found that a modification in which acid is present in the reaction mixture will accelerate the reaction and easily aminomethylate the gamma- and delta-tocopherols. Advantageously, the use of an acidic medium for the aminoalkylation reaction permits the formation of certain amino methylated tocopherol intermediates. In accordance with the process of the instant invention this acid may be added to this reaction mixture in a catalytic amount of from about 0.1% to 5% by volume, separation of the d-alpha-tocopherol from the non-alpha-tocopherol adducts can be facilitated by the use of an acidic solvent medium for the reaction. Using such an acidic solvent and an immiscible non-polar solvent will cause two phases to form as the reaction proceeds. The two phases will be the polar water miscible organic phase containing the non-alpha-tocopherol adducts, and the nonpolar water immiscible phase containing the d-alphatocopherol along with any sterols and fatty acids present. Without using two immiscible solvents the separation of alpha-tocopherol from the adducts will not be achieved. The polar solvent phase can be composed of water miscible mixtures of other solvents such as alcohol, acetonitrile or acetone, and acids. Water may be added to the solvents in order to provide immiscibility. The non-polar, water immiscible phase can likewise be composed of a mixture of solvents.

Separation of alpha-tocopherol from non-alpha-tocopherol adducts is accomplished by partitioning between different organic solvents. The solvents employed are a water miscible polar solvent containing a suitable acid to take up the aminoalkylated tocopherol adducts, and a water immiscible non-polar organic solvent to take up the alphatocopherol along with hydrocarbon imparities such as: residual sterols, fatty acids and hydrocarbons. A liquid organic acid of sufficient acidity may function as both the water miscible polar phase and acid component. The partitioning is preferably carried out as a continuous countercurrent extraction at room temperature, although any convenient procedure and equipment can be used which would accomplish the partitioning of the two phases.

Any of the hydrocarbon solvents such as hexane, octane, toluene, petroleum ether, esters, ethers, alkanes, chlorinated hydrocarbons, etc. and mixtures of solvents can be used for the non-polar solvent which takes up the alphatocopherol. The water miscible, polar solvent which collects the aminoalkylated tocopherol adduct is preferably an alcoholic solvent with mineral acids, a carboxylic acid or similar acidic solvent capable of extracting the tocopherol adducts. Preferably an acid should be used which is capable of forming salts with the amine adducts.

Some preferred polar solutions which will extract the non-alpha-tocopherol amine adducts are solutions made up of methanol or acetonitrile containing an acid such as phosphoric acid, formic acid, acetic acid, hydrochloric acid, and water.

Acetic acid has been found to be particularly well suited for forming salts of the non-alpha-tocopherol adducts, and for crystallizing the salt of the deltatocopherol aminomethylated adduct. Phosphoric acid likewise is well suited for crystallizing from all of the adducts highly stable salts which can be isolated from the solution or reconverted to the amine adduct for hydrogenation to upgrade the homologue as described more fully below. Alternatively, the aminoalkylated tocopherol adduct can be recovered as the intermediate compounds formed with an acid that is strong enough to protonate the amine, such as the mineral acids: phosphonic, hydrochloric, hydrobromic, and sulfuric. Also suitable are the organic acids, i.e. aromatic or aliphatic carboxylic acids, phosphonic, sulfonic and the like which are polar, and which are strong enough to protonate the tocopherol amine. The novel acidic intermediates of the tocopherol amine adducts obtained in this way are the compounds of the formula:

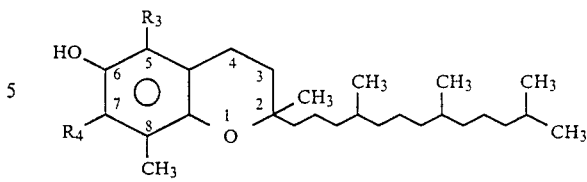

where either $R_3$ or $R_4$ is hydrogen and the other is an aminomethyl group or where $R_3$ or $R_4$ is a methyl group and the other is an aminomethyl group or where both $R_3$ and $R_4$ is an aminomethyl group; and where the aminomethyl groups have the formula:

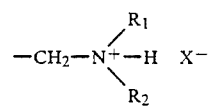

where $R_1$ and $R_2$ are as previously defined and where X is an anionic acid moiety of a water miscible acid. Suitable acids are those having an acid dissociation constant ($pK_3$) of less than 5 such as the water miscible aliphatic, araliphatic or aromatic mono- or di-carboxylic acids, phosphonic acid, sulphonic acid, or inorganic acids such as sulfuric acid, phosphoric acid, or hydrohalic acids (hydrochloric, hydrobromic, hydroiodic). Of the aliphatic carboxylic acids those preferred are the monocarboxylic acids of the formula $R_5COOH$ where R is hydrogen or an alkyl group having 1–4 carbon atoms such as formic, acetic, propionic or butyric acid. Phosphoric aminomethylated tocopherol adducts can be crystallized as salts as can the delta-tocopherol aminomethylated acetate.

In the first process step, i.e. the aminoalkylation reaction, any toco-trienol present in the mixed tocopherol concentrate is also aminoalkylated. The aminoalkylated tocotrienol may be separated from alpha-tocopherol and/or alpha-tocotrienol by extraction with a polar solvent containing acid. Also, like the tocopherol aminomethylated intermediates, the tocotrienol adduct can be upgraded into alpha-tocopherol by subjecting the aminomethylated adduct to reduction.

The starting materials, i.e. the mixed tocopherol homologue concentrates utilized in this reaction may vary depending on individual needs and desires, and upon the particular embodiment of the instant invention used. When, for example, the isolation of natural d-alpha-tocopherol is desired, it might be preferred to use a starting material with a low sterol and fatty acid concentration. Preferably, in fact, the fatty acid concentration in particular should be lower than two percent (2%) by weight, and more preferably, less than one percent (1%) by weight. This low fatty acid concentration serves to ease operations. If, however, one is concerned with the isolation of non-alpha-tocopherols, and upgrading these to d-alpha-tocopherols in high purity, then the sterol and fatty acid concentrations do not necessarily have to be low, since it is possible, using a preferred embodiment of the instant invention, to separate the sterols and fatty acids from the non-alpha-tocopherol aminomethylated adducts by contacting said adducts with an acid capable of protonating the tocopherol amine, thereby forming the aminomethylated adduct salt which separates from the sterols, fatty acids, and isolated d-alpha-tocopherol cut which can be purified by conventional methods. The acids can be used in the aminomethylation reaction as a solvent or catalyst, or could be used to extract already formed aminomethylated adducts. After the salt is formed, and impurities separated, the aminomethylated tocopherol adduct can be regenerated by stripping off the acidic moiety, or, preferably by contact with base. The most preferred bases to liberate the adduct from the adduct salts is, ammonia, or an alkaline or alkali earth hydroxide or oxide. A preferred method to reform the aminomethylated adduct from its salt is to contact it with a base, or extract the salt with a basic solution when the aminomethylated salt is in a non-crystalline form (i.e. when solvated). One of the preferred examples of this is to bubble ammonia through a solution of the salt.

In a preferred method of this invention, wherein the mixed tocopherol concentrated is subjected to an aminomethylation reaction with, for example dimethylamine and formaldehyde, it is most preferred to combine with acetic acid in order to form the acetic acid salts of the dimethylaminomethyl adducts of the non-alpha-tocopherols. These are stable, transportable intermediates which can be stored, and later the acetic acid salts can be readily converted to additional alpha-tocopherol by removing the acetic acid and reducing by hydrogenolysis of the resulting aminomethylated tocopherols to form d-alpha-tocopherol. For best results, it is preferred that the acetic acid be removed entirely prior to hydrogenolysis. This separation can be done by conventional means, as, for example, stripping on a wiped film evaporator, or by stripping with a co-solvent such as toluene. Preferably, the acetic acid should be reduced to a concentration of less than one percent acetic acid in the mixture of aminomethylated tocopherols being reduced by hydrogenolysis. Such removal is preferred since hydrogenolysis yields are higher without acetic acid present. It is however, more difficult, but possible, to reduce the aminomethylated tocopherols with the acetic acid present as a solvent.

When substantial amounts of delta-tocopherol are present in the mixture, the aminomethylation and the subsequent reduction are generally carried out in more than one successive stage where a two stage reduction is being used, the aminomethylation reaction is carried out with from about 1 to about 5 molar equivalents of both dimethylamine and formaldehyde for each molar equivalent of total mixed tocopherols in the reaction mixture. The reaction is continued for from about one-half (½) to two and one-half (2½) hours, preferably about two hours, in order to convert the gamma-, delta-tocopherols and beta-tocopherol to the corresponding aminomethyl derivatives.

The mixture is then subjected to hydrogenolysis, in order to reduce the aminomethyl derivatives to a mixture of d-alpha-tocopherol and beta-tocopherol. The mixture is then aminomethylated, after which the d-alpha-tocopherol product can be separated before the hydrogenolysis is done to upgrade the aminomethylated beta-tocopherol adduct. Preferably, this is done by acidic extraction, forming the salt of the adduct. This can then, if desired, be followed by regeneration of the tocopherol adduct preferably by exposure to a base. Hydrogenolysis then can be carried out to reduce the remaining tocopherol adducts to d-alpha-tocopherol.

The hydrogenolysis is carried out by using a hydrogenolysis catalyst (Pd, Ni, Cu or Pt metal or supported salts), preferably palladium on carbon catalyst, five percent (5%) palladium on carbon being suitable. Also suitable are Raney Ni, supported Ni, $Pd(OH)_2$ on carbon and copper chromite. Hydrogen gas is used, preferably at from 100 to about 1000 lbs/inch$^2$ pressure although hydrogen pressure can acceptably be up to 2500 psi and a temperature of from about 100 to 220° C. for a reaction time of from about 5 minutes to about 2 hours. The reaction preferably uses an organic solvent, such as toluene, alcohol, ethers, esters, alkanes, and the like. Other catalysts, such as nickel or copper chromite and other known hydrogenation catalysts can also be utilized. The preferred method however is to utilize a palladium on carbon catalyst with hydrogen gas.

Any mixture of tocopherols can be aminomethylated, and the alpha separated or the mixture can be reacted directly in another aminomethylated reaction utilizing from 1 to about 10 equivalents of both DMA and formaldehyde for each equivalent of unreacted beta-, gamma-, or delta-tocopherol present, and then subjecting the reaction mixture to hydrogenation in order to convert all of the aminomethyl derivatives to alpha-tocopherol. Any alpha-tocopherol, of course, can be separated before reduction, as previously described.

In a multi-stage hydrogenolysis, the first stage is carried out as previously described, using hydrogen gas, preferably, with a palladium on carbon catalyst. The hydrogenolysis is done with the aminomethylated non-alpha-tocopherol adducts in an organic solvent, preferably toluene and in a temperature range of from about 140° C. to about 200° C. After about one hour the temperature is dropped to about 150° to 175° C. and hydrogenolysis is continued in the presence of added formaldehyde with acetic acid for an additional one to two hours.

Optionally, if it is desired to recover the tocopherol content from a mixed tocopherol source as alpha-tocopherol without a separation step, the tocopherol mixture can be converted to alpha-tocopherol and aminomethylated adducts, which can then be subjected to hydrogenolysis.

These and other readily attainable variations in the novel processes of this invention will be more fully understood from the examples which follow These examples are intended to clarify and demonstrate the instant invention and not to limit it. All parts and percentages are by weight unless otherwise specified.

EXAMPLE I

A soy-derived concentrate of tocopherol with the following composition: 19.4% delta-tocopherol, 40.6% beta-gamma-tocopherol, and 5.7% naturally produced d-alpha-tocopherol was converted to the dimethyl aminomethyl adduct.

300 grams (g) tocopherol concentrate and 120 g 60% dimethylamine aqueous solution were placed in a glass reaction flask and 129 g of 37% formaldehyde was added over ½ hour. At the end of the addition the temperature was raised to 75° C. and held for two hours. The reaction was cooled and 600 milliliters (ml) hexane added and the aqueous layer was separated and discarded. The hexane solution was extracted with 1200 ml and 300 ml of 80% acetic acid. The acetic acid phases were washed countercurrently twice with 300 ml of hexane. Like phases were combined.

The hexane phase was evaporated under aspirator vacuum to yield 100 g of a product containing 0.8% delta-tocopherol, 0.4% beta-gamma-tocopherol, and 11% naturally produced d-alpha-tocopherol.

The acetic acid phase was stripped at 80° C. under aspirator vacuum to remove substantially all of the acetic acid. It was then taken up in 1 liter of hexane and neutralized with dilute KOH, the hexane solution was washed 3 times with water and the hexane removed under vacuum. The extract phase 232 g was dissolved in 250 ml of toluene and charged to an autoclave with 12 g of 5% palladium on carbon catalyst 50% water wet. Hydrogenolysis was carried out at 200° C. for 2 hours at 300 psi hydrogen pressure. The product was cooled, removed from the autoclave, filtered and the solvent removed under vacuum to yield 207 g of a product with the following composition: 0.3% delta-tocopherol, 11.5% beta-gamma-tocopherol, 81.7% d-alpha-tocopherol.

This product was redissolved in 250 ml toluene in a glass reactor, 20 g of 60% dimethylamine added, and 22 g of 37% formaldehyde was added over ½ hour. The temperature was raised to 75° C. and held for 3 hours. The reaction was cooled, the aqueous phase discarded and the toluene solution washed with water one time.

The toluene solution was charged to the hydrogenolysis vessel along with 12 g of 5% palladium on carbon catalyst, 50% water wet, and heated to 200° C. for 2 hrs under 300 psi hydrogen. The reaction was cooled, filtered and the solvent removed under vacuum to yield 201 grams of a product of the following composition: 0.4% delta-tocopherol, 0.4% beta-gamma-tocopherol, and 92.7% d-alpha-tocopherol.

EXAMPLE II

A 281 g quantity of soybean oil concentrate of the following composition: 17.2% by weight delta-tocopherol, 37.1% beta-gamma-tocopherol, and 5.6% alpha-tocopherol was subjected to an aminomethylation reaction with dimethylamine and formaldehyde as described in Example I. Then, 300 g of the aminomethylated product was dissolved in 600 g of octane and the aminomethylated adducts were extracted with 700 ml and 300 ml quantities of 80% acetic acid. The polar acid phases were combined and washed with 300 ml of octane. The 300 ml portion of octane was then combined with the 600 g portion of octane which had been washed with the acetic acid. The octane was evaporated to give 108.2 g of a product containing: 9.1% naturally produced d-alpha-tocopherol, 0.7% delta-tocopherol, and 0.5% beta-gamma-tocopherol, in addition to the fatty acid, sterols and other impurities.

The 300 and 700 ml portions of acetic acid was combined and the acetic acid removed by vacuum stripping to 11.3% by weight acetic acid. This quantity was diluted with 3 volumes of octane and neutralized with calcium oxide. The amount of calcium oxide added was 1.4 moles of calcium oxide per mole of acetic acid. The solution was filtered to remove the calcium salts and stripped under vacuum to remove the octane. The product remaining after the octane was removed was 189.3 g of non-alpha- aminomethylated tocopherol adducts. This 189.3 g quantity was subjected to hydrogenolysis in 200 g of octane for two hours at 200° C. under 200 lbs/sq. inch (psi) of hydrogen with 2.5% by weight adduct of 5% palladium on carbon catalyst. The product recovered had a mass of 165.6 g and was of the following composition: 0.9% delta-tocopherol, 21.4% beta-gamma-tocopherol, and 65.6% d-alpha-tocopherol.

EXAMPLE III

A 150 g quantity of aminomethylated non-alpha-tocopherols, having 14.6% delta-tocopherol adduct and 25.0% betagamma-tocopherol adduct wa dissolved in 600 ml of ethylacetate, and to this 16 ml of phosphoric acid was added dropwise with stirring. The solution was heated to reflux, and cooled to 0° C. A crystalline product of 86 g of the beta-, gamma- and delta-aminomethylated tocopherol phosphate salt formed.

The crystalline product was collected by filtration; and added to 500 ml of toluene. The remaining phosphoric acid was neutralized with aqueous sodium hydroxide, and then the product was subjected to hydrogenolysis, at 200 psi hydrogen for 2 hours at 200° C. using palladium on carbon catalyst.

After hydrogenolysis an analysis of the product derived from the crystalline aminomethylated tocopherol phosphate salt indicated that it had the following composition: 60.8% d-alpha-tocopherol, 21.3% beta-gamma-tocopherol, and 0.2% delta-tocopherol.

In identical procedures, aminomethylated tocopherol concentrate was combined with the following acids: succinic acid, propionic acid, sulfuric acid.

Crystalline products resulted from this combination with the amine adducts.

EXAMPLE IV

A tocopherol concentrate from soybean oil was aminomethylated using dimethylamine and aqueous formaldehyde, as previously described in Example I. The product was then extracted by the addition of aqueous acetic acid (80% acid) as the polar organic phase. Octane was added as the nonpolar water immiscible organic phase. The non-polar organic phase containing naturally produced d-alpha-tocopherol and such impurities as sterols and fatty acids, was separated. The acetic acid was removed by vacuum stripping to provide 1500 g of the aminomethylated tocopherol adducts with an acetic acid content of 7%. This was diluted with 1500 g of toluene. The mixture was placed in a reactor equipped with a dry ice condenser and anhydrous ammonia was added to the solution. The ammonia was added until reflux was observed from the condenser. The product was then filtered to remove the ammonium acetate formed.

The beta-, gamma-, and delta- aminomethylated tocopherol adducts remained in solution. These adducts were thus available for hydrogenolysis. If these adducts were subjected to hydrogenolysis their vitamin activity would be upgraded by the substitution of methyl groups to the ring in the 5/7 position where the aminomethyl group was added.

EXAMPLE V 100 g of a tocopherol concentrate (17% delta, 39% betagamma, 5% alpha), was reacted with 108 g of 26% aqueous dimethylamine, 52 g of 37% formalin at 80°–90° C. for 2½ hours using the procedure outlined in Example I. After this aminomethylation, 100 g of hexane was added and the solution allowed to settle. The aqueous solution was removed and washed with 50 g of hexane. The hexane layers were combined. The hexane solution was extracted with 300 ml of 80% acetic acid. The hexane layer was separated and back extracted with 25 ml of 80% acetic acid. The acetic acid layers were combined and washed with 150 ml of hexane.

The acetic acid layers were combined and the bulk of the acetic acid was removed in vacuo at 80° C. The last amounts of acetic acid was removed by treatment with a 26% aqueous dimethylamine solution to give 71 g of purified tocopherol adduct.

The hexane layers from the above extraction were combined and the solvent removed in vacuo to give 36.6 g of a red oil containing naturally produced d-alpha-tocopherol at the 10.4% by weight level.

To both reduce the adducts and then add a methyl group for further alpha-tocopherol production, a two stage hydrogenolysis was conducted as follows: the 71 g of purified tocopherol adducts were dissolved in 150 ml of toluene, and was put under hydrogen (200 psi) in the presence of 10 g of palladium on carbon (50% water wet) catalyst for two hours at 200° C., at which time the reactor was cooled to 80° C. and vented. To this a suspension of 10 g of acetic acid, 15 g of paraformaldehyde in 150 ml of toluene was added. The reactor was repressurized to 200 psi with hydrogen and reacted for 2 hours at 160° C. The reaction was cooled to room temperature and discharged from the reactor. The catalyst was removed by filtration and solution was washed with water. The toluene was removed in vacuo to give 64.2 g of an oil, 88.3% d-alpha-tocopherol (92% yield).

EXAMPLE VI

A 600 g mixture of alpha-, beta-, gamma-, and deltatocopherols was added to 360 ml of glacial acetic acid followed by the slow addition of 270 ml of aqueous 60% dimethylamine, to this 270 ml of aqueous 37% formaldehyde was added to this mixture and the reaction mixture was stirred for about two hours at temperatures in the range of from 85° to 90° C. 600 ml of octane was then added and the reaction mixture was permitted to settle. The aqueous phase was then removed.

230 g of the octane-product mixture was then diluted with 100 g of hexane. This mixture was extracted with 250 g of 80% acetic acid. The hexane layer, which also contained sterols and fatty acid impurities along with the naturally produced d-alpha-tocopherol, was separated and extracted with a second portion of 100 g of 80% acetic acid. The acid layers containing dimethylaminomethylated tocopherol were combined and extracted with 100 g of hexane. The hexane portions were combined and stripped by vacuum of the solvent to give 45 g of raffinate having approximately 13% alpha-tocopherol. The beta-, gamma-, and delta- adducts contained in the polar acetic acid portion was then subjected to vacuum stripping at less than 80° C. to remove the solvent The resulting dimethylaminomethylated oil product collected was washed twice with 25% sodium hydroxide to remove the remaining amounts of acetic acid, which freed the beta-, gamma-, and delta- aminomethylated tocopherol adducts from association with acetate. The organic layer was then combined with 100 g of hexane and washed with water. The hexane was then removed under vacuum, and 100 g of toluene was added to the oil product. This solution was hydrogenated for two hours under 200 psi hydrogen at 200° C. with 5 g of 5% palladium on carbon catalyst which was 50% water wet. After filtering the catalyst and removing the solvent under vacuum, 53 g of a product was obtained which was 88% dalpha-tocopherol as analyzed by gas liquid chromatography.

We claim:

1. A process for separating d-alpha tocopherol from a mixture of d-alpha tocopherol and the aminomethyl adduct of non-alpha tocopherol homologues comprising:

contacting said mixture with a water immiscible non-polar solvent and a water miscible polar solvent and an acid whereby two phases are formed wherein the polar solvent phase contains the acid salts of the aminomethylated non-alpha tocopherols and said non-polar phase contains the d-alpha tocopherol and separating said phases into an alpha-tocopherol fraction and a non-alpha tocopherol amine adduct fraction.

2. A process as described in claim 1 wherein after separation said non-alpha-tocopherol fraction is subjected to hydrogenolysis to convert said aminomethyl adduct to alpha-tocopherol.

3. A process as defined in claim 2 wherein said hydrogenolysis is conducted with hydrogen in the presence of a hydrogenation catalyst.

4. A process as defined in claim 1 wherein said acid forming said acid salt of said amine adduct is a water miscible acid having an acid dissociation constant $pK_a$ less than 5.

5. A process as defined in claim 1 wherein said acid is selected from the group consisting of aliphatic monocarboxylic acid of the formula $R_5COOH$ where $R_5$ is hydrogen or an alkyl group having 1–4 carbon atoms and phosphonic acid, sulfonic acid, phosphoric acid, sulfuric acid or an hydrohalic acid.

6. A process as defined in claim 5 wherein said acid is acetic acid.

7. A process as defined in claim 5 wherein said acid is phosphoric acid.

8. A process for obtaining naturally derived alpha-tocopherol from a tocopherol concentrate containing a mixture of tocopherols comprising:

(a) aminomethylating said concentrate to convert any non-alpha-tocopherol products contained in said concentrate to the corresponding aminomethylated non-alphatocopherol adduct and converting said amine adducts to the acid salt;

(b) contacting the product from (a) containing the non-alpha-tocopherol amine adduct with a water miscible polar solvent and a water immiscible non-polar organic solvent to provide two phases wherein said non-polar solvent phase contains any alpha-tocopherol present and said polar solvent phase contains said non-alpha-tocopherol amine adducts;

(c) separating said phases to provide a non-polar alpha-tocopherol fraction and a polar non-alpha-tocopherol amine adduct fraction;

(d) reducing said non-alpha-tocopherol amine adduct to alpha-tocopherol; and (e) recovering said alpha-tocopherol.

9. A process as defined in claim 8 wherein said acid salts are formed during said aminomethylation.

10. A process as defined in claim 8 wherein said acid salts are formed subsequent to said aminomethylation by addition of acid during formation of said two phases by contact with said polar and non-polar solvents.

11. A process as defined in claim 8 wherein said amine adduct is reformed from said acid salt prior to reduction of said non-alpha-tocopherol amine adduct to alphatocopherol.

12. A process as defined in claim 8 wherein said aminomethylation is conducted by reaction of said tocopherol concentrate with dimethylamine and formaldehyde to provide aminomethyl adducts of any non-alpha-tocopherol present in said concentrate.

13. A process as defined in claim 12 wherein said acid salt is the acetic acid salt.

14. A process as defined in claim 8 wherein said reduction of said non-alpha-tocopherol amine adduct to alpha-tocopherol is accomplished by hydrogenolysis of said amine adduct with hydrogen in the presence of a hydrogenation catalyst.

15. A process as defined in claim 8 wherein said tocopherol concentrate contains alpha-tocopherol admixed with a non-alpha-tocopherol selected from the group consisting of beta-, gamma-, delta-tocopherol and mixtures thereof.

16. A process as defined in claim 8 wherein the steps of (a), (b), (c), and (d) are repeated prior to conducting step (e).

17. A process as defined in claim 8 wherein a two stage hydrogenation reduction is conducted on said non-alpha-tocopherol amine adduct.

* * * * *